US00PP26673P3

(12) United States Plant Patent
Jansen

(10) Patent No.: US PP26,673 P3
(45) Date of Patent: Apr. 26, 2016

(54) ***PENSTEMON* PLANT NAMED 'CHA CHA PINK'**

(50) Latin Name: ***Penstemon* hybrid**
Varietal Denomination: Cha Cha Pink

(71) Applicant: Terra Nova Nurseries, Inc., Canby, OR (US)

(72) Inventor: Robert D. Jansen, Naalehu, HI (US)

(73) Assignee: Terra Nova Nurseries, Inc., Canby, OR (US)

( * ) Notice: Subject to any disclaimer, the term of this patent is extended or adjusted under 35 U.S.C. 154(b) by 139 days.

(21) Appl. No.: 14/120,090

(22) Filed: Apr. 24, 2014

(65) Prior Publication Data

US 2015/0313072 P1 Oct. 29, 2015

(51) Int. Cl.
*A01H 5/02* (2006.01)

(52) U.S. Cl.
USPC ..... Plt./465

(58) Field of Classification Search
USPC ..... Plt./465
See application file for complete search history.

*Primary Examiner* — Keith Robinson
(74) *Attorney, Agent, or Firm* — Klarquist Sparkman, LLP

(57) ABSTRACT

A new and distinct cultivar of *Penstemon* plant characterized by medium size rose pink flowers in dense clusters, long bloom time, a compact, upright, well branched habit, with multiple crown from the base, clean-looking, deep green, attractive foliage, and excellent vigor.

1 Drawing Sheet

Botanical denomination: *Penstemon* hybrid.
Variety designation: 'Cha Cha Pink'.

BACKGROUND OF THE INVENTION

The present invention relates to a new and distinct cultivar of *Penstemon*, given the name, 'Cha Cha Pink'. *Penstemon* is in the family Scrophulariaceae. This plant originated a controlled breeding plan to create a compact, upright, medium size, multiflowered series. The exact parents are unknown, unnamed proprietary plants. This cultivar was selected for its compact growing habit, medium size flowers in dense clusters, long flowering time, vigor, and clean attractive look. It is an ideal plant for a sunny border in full sun.

Compared to *Penstemon* 'Strawberry Taffy', U.S. Plant Pat. No. 22,569, the new cultivar is shorter and has smaller flowers in tighter clusters, and narrower leaves.

Compared to *Penstemon* 'Hidcote Pink', an unpatented plant, the new cultivar is shorter, with smaller, narrower leaves, and the flowers are a little darker and have a dark line above the bee tracks on the lower three lobes.

*Penstemon* 'Cha Pink' is uniquely distinguished by its:

1. medium size rose pink flowers in dense clusters,
2. long bloom time,
3. compact, upright, well branched habit, with multiple crown from the base,
4. clean-looking, deep green, attractive foliage, and
5. excellent vigor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the new cultivar on a 7-month-old plant in bloom in mid-June in Canby, Oreg.

FIG. 2 shows the habit on a 7-month-old plant growing in the garden in Canby, Oreg.

DETAILED PLANT DESCRIPTION

The following is a detailed description of the new *Penstemon* cultivar based on observations of 18 month-old specimens grown outside in five gallon containers in full sun in Canby, Oreg. in October. The color descriptions are all based on The *Royal Horticultural Society Colour Chart,* 5$^{th}$ edition, 2007.

Plant:

*Type*.—Herbaceous perennial.
*Form*.—Upright, branching.
*Cold hardiness*.—USDA Zone 7-10.
*Size*.—Grows to 70 cm wide and 50 cm high.
*Vigor*.—Excellent.
*Stem number*.—About 12 main stems from the crown.
*Stem*.—Upright, grows to 40 cm long and 1 cm wide (at the base), glabrous at base to glandular pubescent toward peduncle, internodes grow to 2 cm long, Yellow Green 146C.
*Roots and rooting*.—Fibrous root system, While 155C, roots easily from stem cuttings in 10 to 14 days.

Leaf:

*Type*.—Simple.
*Arrangement*.—Opposite.
*Shape*.—Lanceolate.
*Venation*.—Pinnate, main vein on top and bottom side Yellow Green 146C.

*Margins*.—Serrulate.
*Apex*.—Acuminate.
*Base*.—Attenuate, clasping.
*Blade size*.—Grows to 8 cm long and 2 cm wide (near inflorescence), to 7 cm long and 14 mm wide on stem.
*Surface texture*.—Glabrous on both sides.
*Petiole*.—None, sessile.
*Leaf color*.—Topside Green 137A, bottom side closest to Yellow Green 147A.

Inflorescence:
*Type*.—Terminal, many flowered, dense thyrse.
*Number of flowers per inflorescence*.—32 to 64.
*Size of inflorescence*.—Grows to 24 cm long and 11 cm wide.
*Peduncle*.—Strong, semi-upright, grows to 2 cm long and 3.5 mm wide, pubescent, Yellow Green 146C.
*Pedicel*.—Medium strength, grows semi-upright to 6 mm long and 1.5 mm wide, pubescent, Yellow Green 146C.
*Bloom period*.—Mid June to frost in October in Canby, Oreg. if spent flowers are removed.

Flower bud:
*Size*.—3 cm long and 11 mm wide.
*Description*.—Closed tubular, bulging, flattened ventrically, pubescent.
*Color*.—Red Purple 61A with tip 61B and bottom side tube White 155C.

Flower:
*Type*.—Zygomorphic, perfect.
*Shape*.—Tubular, bilabiate.
*Size*.—Grows to 4 cm long and 3.4 cm wide.
*Corolla description*.—Grows to 4 cm long and 3.4 cm wide; tube is bulbous in the calyx for 6 mm long and 5 mm wide, narrowing then widening for 25 mm and flaring to 34 mm wide, 5 lobes, the two smaller top lobes flare back (each 12 mm wide and to 11 mm deep) and two larger lateral 12 mm wide and 14 mm deep, and the lower lobe 13 mm wide and 11 mm deep, lobe margins entire to slightly jagged, tips obtuse; outside glandular pubescent, inside sparsely pubescent; outside color topside tube Red Purple 71B, bottom side tube White NN155C, lobes Red Purple 61C; inside color: lobes Red Purple 61C on outside ¾, lower 3 lobes edged Red Purple 72A, tube White NN155D with bee tracks on lower 3 lobes Red Purple 72A.
*Calyx description*.—9 mm deep and 8 mm wide, 5 overlapping lobes cut to the base, each lobe broadly ovate in shape, 9 mm deep and 4 mm wide, margins entire, tip acuminate, base cuneate, outside Yellow Green 146C with tip Greyed Purple 187A, inside Yellow Green 146C, glabrous inside and glandular pubescent outside.
*Pistil description*.—1, 30 mm long, ovary 5 mm long and 2 mm wide, Yellow Green 146D; style 25 mm long and less than 1 mm wide, style White N155A darkening near tip Purple 72A, stigma shape conical, White NN155C.
*Stamen description*.—5, one sterile without an anther, held within the corolla 30 mm long, filaments 23 to 29 mm long and White NN155C, anthers oval, 2 mm long, Greyed Purple 187B, pollen amount moderate, White NN155C.
*Fragrance*.—None.
*Lastingness*.—A flower lasts 5 to 6 days.

Fruit:
*Type*.—Capsule.
*Texture*.—Pubescent.
*Fertility*.—Good.
*Size*.—7 mm deep and 1 mm wide.
*Color*.—Brown N199C.

Seed:
*Shape*.—Irregular.
*Texture*.—Glabrous.
*Size*.—2 mm long.
*Color*.—Brown 200A.

Pests and diseases: The new cultivar is typical to the genus. No problems have been found in Canby, Oreg.

I claim:

1. A new and distinct cultivar of *Penstemon* plant substantially as shown and described.

* * * * *

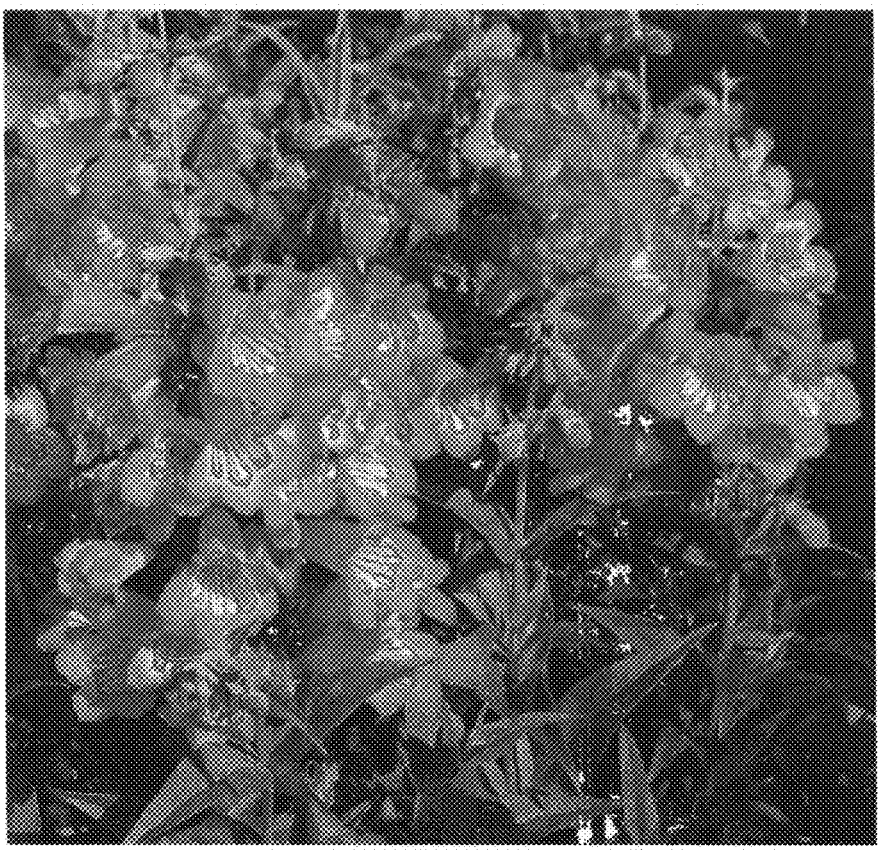
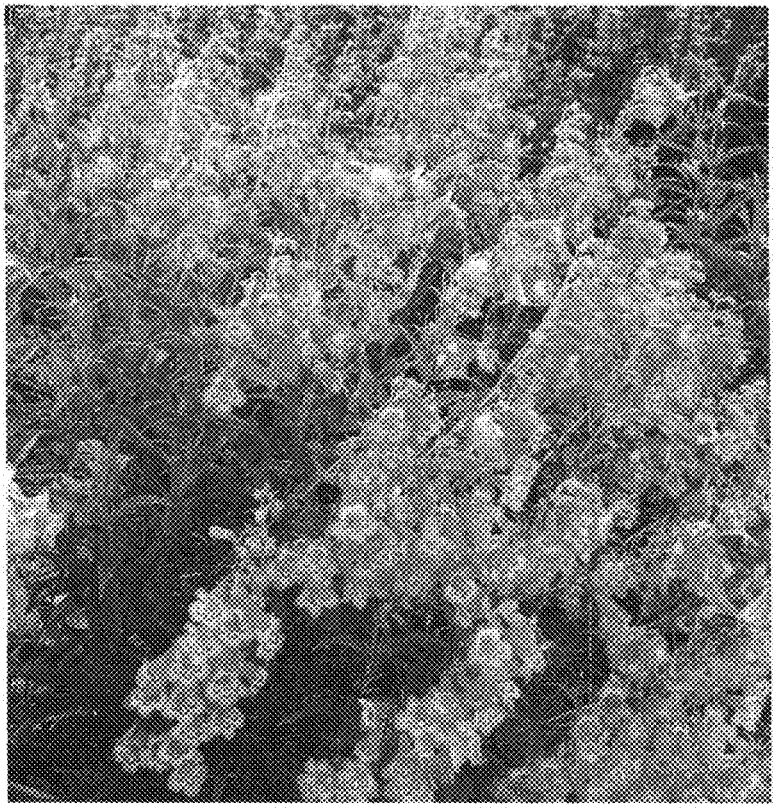
FIG.1 above left
FIG. 2 on left